(12) United States Patent
Wicklein

(10) Patent No.: US 10,521,934 B2
(45) Date of Patent: Dec. 31, 2019

(54) METHOD, X-RAY UNIT AND COMPUTER PROGRAM PRODUCT FOR DETERMINING A THREE-DIMENSIONAL IMAGE DATA SET

(71) Applicant: SIEMENS HEALTHCARE GMBH, Erlangen (DE)

(72) Inventor: Julia Wicklein, Neunkirchen A. Br. (DE)

(73) Assignee: Siemens Healthcare GmbH, Erlangen (DE)

( * ) Notice: Subject to any disclaimer, the term of this patent is extended or adjusted under 35 U.S.C. 154(b) by 14 days.

(21) Appl. No.: 15/876,359

(22) Filed: Jan. 22, 2018

(65) Prior Publication Data

US 2018/0211421 A1 Jul. 26, 2018

(30) Foreign Application Priority Data

Jan. 20, 2017 (DE) .......................... 10 2017 200 930

(51) Int. Cl.
*G06K 9/00* (2006.01)
*G06T 11/00* (2006.01)
*G06T 7/12* (2017.01)
*A61B 6/02* (2006.01)
*A61B 6/00* (2006.01)
*G06T 7/00* (2017.01)
*G06T 5/30* (2006.01)
*G06T 5/50* (2006.01)

(52) U.S. Cl.
CPC ............ *G06T 11/006* (2013.01); *A61B 6/025* (2013.01); *A61B 6/502* (2013.01); *A61B 6/5258* (2013.01);

(Continued)

(58) Field of Classification Search
CPC ....... A61B 6/025; A61B 6/502; A61B 6/5258; G06T 11/006; G06T 2207/10116; G06T 2207/30068; G06T 7/0012; G06T 7/12
See application file for complete search history.

(56) References Cited

U.S. PATENT DOCUMENTS

| | | | | |
|---|---|---|---|---|
| 2006/0285737 A1* | 12/2006 | Hamill | .................. | G06T 11/008 382/131 |
| 2008/0152203 A1* | 6/2008 | Bal | ....................... | G06T 11/008 382/131 |
| 2015/0029178 A1* | 1/2015 | Claus | ..................... | A61B 6/032 345/419 |

OTHER PUBLICATIONS

Zhang, Zhaoxia, et al. "Metal artifacts reduction for tonnosynthesis." 2014 IEEE 11th International Symposium on Biomedical Imaging (ISBI). IEEE, 2014.*

(Continued)

*Primary Examiner* — Avinash Yentrapati
(74) *Attorney, Agent, or Firm* — Laurence Greenberg; Werner Stemer; Ralph Locher

(57) ABSTRACT

A method for determining a three-dimensional image data set from a plurality of two-dimensional projection images of an object under examination applies at least one morphological operation to each projection image in order to provide a processing image associated with the respective projection image. At least one respective imaging segment is segmented, in which a highly absorbent region is mapped, depending on the associated processing image, and a respective mask image is generated in which pixels belonging to the imaging segment are marked. An associated synthetic image for each projection image is determined, the image data of which within the imaging segment is set to predetermined values. The projection images and the synthetic images are separately filtered. The three-dimensional image data set is determined by backprojecting the mask images to determine a mask value for each voxel of the image data set.

14 Claims, 4 Drawing Sheets

(52) U.S. Cl.
CPC ............... *G06T 5/30* (2013.01); *G06T 5/50* (2013.01); *G06T 7/0012* (2013.01); *G06T 7/12* (2017.01); *G06T 2207/10116* (2013.01); *G06T 2207/20224* (2013.01); *G06T 2207/30068* (2013.01)

(56) References Cited

OTHER PUBLICATIONS

Meyer, Esther, et al. "Normalized metal artifact reduction (NMAR) in computed tomography." Medical physics 37.10 (2010): 5482-5493.*

Abdurahman, Shiras, et al. "Out-of-plane artifact reduction in tomosynthesis based on regression modeling and outlier detection." International Workshop on Digital Mammography. Springer, Berlin, Heidelberg, 2012.*

Zhang, Zhaoxia, et al. "Metal artifacts reduction for tonnosynthesis." 2014 IEEE 11th International Symposium on Biomedical Imaging (ISBI). IEEE, 2014. (Year: 2014).*

Esther Meyer, et al.; "Normalized Metal Artifact Reduction (NMAR) in Computed Tomography "; Med. Phys. 37; Oct. 2010; pp. 5482-5493; vol. 10; DOI: 10.1118/1.3484090.

Shiras Abdurahman, et al.; "Out-of-Plane Artifact Reduction in Tomosynthesis Based on Regression Modeling and Outlier Detection"; IWDM 2012; lncs 7361; pp. 729-736; Springer-Verlag Berlin Heidelberg.

Zhaoxia Zhang, et al.; "Metal Artifacts Reduction for Tomosynthesis"; 2014; pp. 513-516; IEEE; Electronic ISBN: 978-1-4673-1961-4.

* cited by examiner

METHOD, X-RAY UNIT AND COMPUTER PROGRAM PRODUCT FOR DETERMINING A THREE-DIMENSIONAL IMAGE DATA SET

CROSS-REFERENCE TO RELATED APPLICATION

This application claims the benefit, under 35 U.S.C. § 119, of German patent application DE 10 2017 200 930.6, filed Jan. 20, 2017; the prior application is herewith incorporated by reference in its entirety.

BACKGROUND OF THE INVENTION

Field of the Invention

The invention relates to a method for determining a three-dimensional image data set from a plurality of two-dimensional projection images of an object under examination. In addition the invention relates to an X-ray unit, a computer program and an electronically readable data medium.

With regard to the reconstruction of three-dimensional image data sets from two-dimensional projection images, very marked differences in contrast in the projection images can result in image artifacts. Corresponding image artifacts are then particularly strongly pronounced if only a relatively small number of projection images, the scanning geometries of which sweep only a limited angular range, are available. In the field of X-ray imaging this is relevant in particular in the area of tomosynthesis methods, for example in the field of 3D mammography. Corresponding artifacts can however also occur in the case of computed tomography or other imaging methods based on projection images.

In the area of X-ray imaging and in particular in the area of mammography corresponding marked differences in contrast occur particularly in the situation when highly absorbent objects are located in the imaging area. In particular, metal parts or calcifications, in other words deposits of calcium salts, exhibit an X-ray absorption differing significantly from tissue and can thus lead to image artifacts. Corresponding artifacts can for example result from a filtering which is performed as part of a filtered backprojection for the purpose of image reconstruction. On account of the filtering, undershoots can occur in the image directly adjacent to the highly absorbent regions. In addition, artifacts can also occur in slices in which no highly absorbent region is located. Said artifacts can result from the fact that parts of the projection images indicate a presence of a highly absorbent region for some of the voxels, while other projection images show the presence of normal tissue for the same voxel. For example, intensity oscillations can occur and/or striation and/or local errors can result in the slice images.

A multiplicity of approaches are known for reducing corresponding artifacts. One possible means of reducing artifacts is to choose an iterative reconstruction approach instead of a filtered backprojection. Corresponding reconstruction approaches are however compute-intensive and have numerous free parameters, which means that a robust and sufficiently fast reconstruction is not possible in all application scenarios.

An approach for artifact reduction is known from the article E. Meyer et al., "Normalized metal artifact reduction (NMAR) in computed tomography", Medical Physics 37, 5482 (2010), in which firstly a preliminary three-dimensional image data set is calculated in which metal objects are segmented by specifying intensity limit values. These segments are subsequently projected forward into the sinograms and the regions determined in this manner are filled with interpolated points. This use of an iterative reconstruction does however increase the computing requirement.

An approach for artifact avoidance is known from the article S. Abdurahman et al., "Out-of-Plane Artifact Reduction in Tomosynthesis Based on Regression Modeling and Outlier Detection", Proc. IWDM, LNCS 7361, pp. 729-736 (2012), which is based on the fact that widely deviating measurement values resulting from statistical tests are not taken into consideration. This approach successfully reduces artifacts from calcifications which lie outside the slice currently under consideration. Compared therewith, an improved means for eliminating metal artifacts is however desired. The above procedure moreover has the disadvantage that all the projection images must already be present prior to the correction, which can be disadvantageous with certain tomosynthesis methods.

It is known from the article Z. Zhang et al., "Metal Artifact Reduction in Tomosynthesis Imaging", Proc. SPIE, Vol. 9412, 94125A (2015) to segment regions in which metal objects are located directly in the projection images. To this end an edge detection is firstly performed and the segmentation takes place subsequently by means of a region growing algorithm. Subsequently the projection images and modified versions of the projection images in which the metal regions are masked are reconstructed separately and the reconstruction results are merged. This type of metal artifact avoidance achieves good results in the area of the monitoring of orthopedic operations. With regard to an avoidance of artifacts which result from relatively small highly absorbent regions, for example calcifications, there is however room for further improvement.

SUMMARY OF THE INVENTION

It is accordingly an object of the invention to provide a method for determining three-dimensional image data sets which overcomes the above-mentioned and other disadvantages of the heretofore-known devices and methods of this general type and which provides for a method for reducing artifacts in three-dimensional image data arising from highly absorbent regions in an object under examination, which method can be realized with a minimal computing requirement and in particular is improved in comparison in respect of the elimination of artifacts that are produced by relatively small metal parts or calcifications.

With the foregoing and other objects in view there is provided, in accordance with the invention, a method for determining a three-dimensional image data set from a plurality of two-dimensional projection images of an object under examination, the method comprising the following steps:

applying at least one morphological operation to each projection image in order to provide a processing image respectively associated with each projection image;

segmenting at least one respective imaging segment, in which a highly absorbent region of the object under examination is mapped in a respective projection image, depending on the processing image associated with the projection image, and creating a mask image associated with the respective projection image, in which pixels belonging to the imaging segment are marked;

generating an associated synthetic image for each projection image, the image data of which outside the imaging segment corresponds to the image data of the associated projection image and the image data of which within the imaging segment is set to predetermined values;

separately filtering the projection images and the synthetic images;

determining the three-dimensional image data set by backprojecting the mask images in order to determine a mask value for each voxel of the image data set, wherein:

when a selection condition dependent on the mask value of the voxel is satisfied, the image data of the respective voxel are determined by a backprojection of the relevant pixels of the filtered projection images; or when the selection condition is not satisfied, the image data of the respective voxel are determined by a backprojection of the relevant pixels of the filtered synthetic images.

In other words, the objects are achieved according to the invention by a method of the type cited in the introduction, which comprises the following steps:

application of at least one morphological operation to each projection image in order to provide a processing image associated with the respective projection image;

segmentation of at least one respective imaging segment, in which a highly absorbent region of the object under examination is visualized in a respective projection image, depending on the processing image associated with said projection image, and creation of a mask image associated with the respective projection image, in which pixels belonging to the imaging segment are marked;

determination of an associated synthetic image for each projection image, the image data of which outside the imaging segment corresponds to the image data of the associated projection image and the image data of which within the imaging segment is set to predetermined values;

separate filtering of the projection images and of the synthetic images;

determination of the three-dimensional image data set, wherein the mask images are backprojected in order to determine a mask value for each voxel of the image data set, wherein the image data of the respective voxel is determined by means of backprojection of the relevant pixels of the filtered projection images when a selection condition dependent on the mask value of said voxel is satisfied, and by means of backprojection of the relevant pixels of the filtered synthetic images when the selection condition is not satisfied.

According to the invention it proposed to segment highly absorbent regions of the object under examination in the projection images. Since a direct segmentation by way of a limit value comparison is not generally possible, according to the invention a procedure is proposed which is based on a preprocessing with the aid of morphological operations. By means of corresponding morphological operations a type of background image can be generated as a processing image, as will be explained in more detail below, which means that highly absorbent regions can be recognized and segmented particularly easily.

The proposed type of segmentation ensures that even calcifications and relatively small metal parts can be segmented reliably and with a relatively minimal computing requirement directly in the projection images. In principle it would also be possible to modify the method according to the invention in such a manner that any other desired segmentation methods are used for segmentation of the highly absorbent regions in the projection images, whereby it would be possible to dispense with the step of applying the morphological operation and the segmentation could take place independently of the processing images. In many application situations, in particular in the area of mammography, the proposed procedure does however enable a particularly efficient artifact reduction.

A central idea of the method according to the invention is that a decision is taken for each individual voxel as to whether for the reconstruction thereof image data of the projection image itself or of a synthetic image derived therefrom is used. In the synthetic images the image data in the imaging segment is discarded and these regions are otherwise populated—as will be explained in detail below.

In order to decide which data source should be used for the reconstruction of the individual voxels a mask value is considered which is determined by means of backprojection of a mask image calculated within the scope of the segmentation. By this means it is possible to check which proportion of the image regions or pixels of the projection images used for determining the intensity of a corresponding voxel lie in imaging segments in which highly absorbent regions of the object under examination are visualized. If said proportion is relatively high, then this voxel probably actually lies in a region in which the object is highly absorbent and in which for example a metal part or a calcification is present. Accordingly, image data of the projection images can be used because this maps the corresponding objects. If it is ascertained however that no image data used for determining the voxel value or only a small part of said image data originates from corresponding imaging segments, then the synthetic images can be used for the reconstruction because the relevant image regions are also contained unchanged in said synthetic images and when the synthetic images are used sudden marked differences in contrast and thus the formation of artifacts can be avoided. It is thus possible in the method according to the invention to significantly reduce or even completely avoid an artifact formation arising from highly absorbent regions with a relatively minimal computing requirement and only a single reconstruction of the three-dimensional image data set.

Morphological operations are basically known in the prior art and will not therefore be explained in detail. Morphological operations can be applied both to binary images and also to grayscale images. The fundamental operations are so-called erosion, which erodes the surface of objects in the image, and so-called dilation, which dilates objects and can result in a merging of previously separate objects. By means of concatenating these operations it is possible to open structures, where for example thin bridges are removed, and to close structures, in order for example to close holes in structures.

By preference, in the method according to the invention morphological operations are used in order to remove the visualization of the highly absorbent regions from the projection images and thereby to generate a type of background image as a processing image. The size of the objects to be removed from the processing image can be predetermined by choosing a corresponding structure element. If the highly absorbent regions are represented as positive contrast in the projection images, they can for example be removed by means of an erosion operation or an opening operation with a correspondingly chosen structure element. In spite of the removal of structures of the size of the highly absorbent regions, fairly large background structures which for example result from differing absorptions in tissue do however remain, and thus a type of background of the projection image, where not only the size but also the shape of the objects to be removed from said background can be predetermined through a choice of corresponding structure elements.

A segmentation can for example take place by subtracting the processing image from the projection image and a segmentation subsequently takes place on the basis of a limit value comparison because influences of differently absorbing tissue can be largely avoided as a result of the background subtraction. By this means a high-quality segmentation of the imaging segments is achieved with a minimal computing requirement. As will be explained in detail below, said segmentation can be further improved if the result of an edge detection is additionally taken into consideration.

As a mask image it is possible in particular to create an image, the pixels of which exhibit a first value outside of imaging segments, in particular 0, and a second value within imaging segments, in particular 1. The mask image can be saved as a digital bit mask in which one bit is assigned to each pixel. The mask value calculated by backprojection of the mask images for the individual voxels can specify for how many or for which proportion of the projection images the pixels backprojected into the voxel are situated in an imaging segment. Those pixels of the projection images or synthetic images, on the image data of which the image data of the respective voxel depends, are considered to be relevant pixels.

The filtering of the projection images and of the synthetic images can correspond to a filtering such as is used for a filtered backprojection which is usual in the prior art. In this situation a ramp filter can in particular be applied to the projection images or synthetic images. With marked differences in contrast such filters result in undershoots and oscillations in the filtered images, which is why in the method according to the invention the synthetic images, in which corresponding marked differences in contrast are reduced or suppressed by the prior replacement of the pixels in the imaging segments, are used for the reconstruction of voxels in regions which are not expected to be highly absorbent.

The selection condition can be satisfied in the situation when for at least a predetermined number of projection images the pixels of the respective projection image which are relevant to the calculation of the image data of the voxel are situated within the respective imaging segment, where the predetermined number is less than the total number of projection images. The predetermined number can in particular lie between 70% and 90% of the total number of projection images, in particular 80% of the total number of projection images. This number can be predetermined by a corresponding choice of a limit value for the mask value. If an ideal visualization could be assumed in the method according to the invention, an optimum reconstruction would be achieved if the selection condition were exclusively satisfied if all the pixels relevant to the reconstruction of the voxel lie within respective imaging segments of the projection images because only in this case is the corresponding voxel actually situated in a highly absorbent region. A highly absorbent region would namely absorb the X-ray radiation passing through it for all the projection images. Since however in the case of real measurement applications the association of some pixels with imaging segments is potentially not correctly recognized on account of noise and other imaging errors, in the method according to the invention the aforementioned lower limit values can preferably be used.

The values to which the image data of the synthetic image are set within the imaging segment can preferably be predetermined by superimposing a noise signal on predetermined initial values for the individual pixels in the imaging segment. As already mentioned, with regard to the recording of projection images it is to be expected that these will exhibit a certain image noise. If a specific image region were not to exhibit said image noise then, in particular if said region has sharp edges, additional image artifacts may result. The latter are avoided by the superimposition of a correspondingly chosen noise signal. In this situation the noise signal should correspond in the ideal case to the image noise both in respect of its frequency distribution and also in respect of its amplitude. To this end, a noise pattern can for example be recorded without an object under examination. It is also possible to generate a corresponding noise signal synthetically. For example, white noise or a high-pass or low-pass filtered noise can be used.

The values to which the image data of the synthetic image are set within the imaging segment or the initial values can be predetermined depending on image data of at least one pixel, adjacent to the imaging segment, of the associated projection image. In particular, an interpolation between a plurality of adjacent pixels can take place. Through this procedure, artificial marked differences in contrast in the synthetic images are avoided, which means that artifact formation in the resulting three-dimensional image data set can be reduced or avoided.

For artifact reduction it is advantageous if marked differences in contrast in the synthetic images are largely avoided. In order to achieve this, it is advantageous if it is ensured that the edges of those regions of the projection images in which a highly absorbent region is mapped are associated with the respective imaging segment during the segmentation. An edge detection can therefore be performed in the projection images in order to provide an edge image associated with the respective projection image, where the segmentation of the imaging segment takes place depending on the edge image associated with the respective projection image. The edge detection can take place for example by means of a Canny algorithm. Any other desired edge detection algorithms can however also be used.

The edge image can be evaluated in such a manner that those image regions in which edges have been recognized and which are situated close to an imaging segment, in other words for example less than a predetermined minimum distance, are added in addition to the imaging segment. One way of achieving this is to mark in a work image both those regions which have already been recognized independently of the edge detection as belonging to the imaging segment, for example by means of the limit value comparison explained in the introduction, and also the edges. Subsequently, edges which are situated close to corresponding regions can be added thereto by means of morphological operations. A closing operation for example can be used for this purpose.

In order to prevent specific structures of the object under examination, for example a skin line of a patient, from being recognized as edges, a limit value comparison can be performed within the scope of the edge detection, in particular following a gradient formation, in order to discard edges having low contrast.

In the method according to the invention it can be advantageous if within the scope of the segmentation of the imaging segments exclusively imaging segments which exhibit a predetermined minimum size are segmented. This can be advantageous because very small, relatively highly absorbent objects, for example microcalcifications, as a general rule generate no or only negligible artifacts. If the latter are excluded during the segmentation, then unnecessary changes to the measurement data are avoided. An exclusion of small segments can be carried out by first performing a preliminary segmentation, whereafter segments which are smaller than a predetermined area or pixel count are discarded.

The projection images can be recorded within the scope of a tomosynthesis method, in particular within the scope of a 3D mammography. With regard to the three-dimensional image data set determined, this can be a result data set from a tomosynthesis method, in particular from a 3D mammography. In this case the method according to the invention can thus also be regarded as a method for performing a tomosynthesis, in particular a 3D mammography.

The projection images can be recorded at various imaging angles with respect to the object under examination, where within the scope of recording the projection images an imaging angle range of less than 90°, in particular of less than 60°, is swept. Correspondingly low imaging angle ranges are advantageous because relatively simple measurement devices can be used. This is for example advantageous in the situation when the recording equipment is intended to be used for mammography screening. A restriction of the imaging angle range is also advantageous in the case of use for monitoring a medical procedure. In the case of C-arm equipment and mammography equipment the imaging angle range may be restricted on account of the construction of the recording equipment.

Within the scope of the method according to the invention it is possible that a two-dimensional image display is produced depending on the three-dimensional image data set, where the highly absorbent region in the two-dimensional image display is graphically highlighted. This can be done for example by displaying the highly absorbent region in a different color, marking with a margin, enhancing the contrast, or the like. The two-dimensional image display can be an artificial projection and/or a slice image. The two-dimensional image display can for example be displayed on a display device and/or otherwise output and/or saved.

A corresponding highlighting of the highly absorbent regions can be advantageous within the scope of the image interpretation. Corresponding highlighting can be effected particularly simply in the method according to the invention because corresponding regions have already been recognized during the evaluation of the selection condition.

In addition to the method according to the invention the invention relates to an X-ray unit having an imaging facility for capturing projection images of an object under examination from a plurality of imaging angles and a control unit, where the control unit is designed in order to perform the method according to the invention. The X-ray unit can in particular be a facility for 3D mammography. This can comprise a stationary X-ray detector and an X-ray source which can be moved or pivoted in relation thereto. In order to reduce the thickness of the tissue to be transirradiated it is possible to additionally provide a compression plate, between which and the detector or a further compression plate a breast to be examined can be compressed. It is however also possible that the X-ray unit is for example a C-arm X-ray unit or a computed tomograph.

The invention furthermore relates to a computer program which can be loaded directly into a memory of a control unit of an X-ray unit, having program resources in order to perform the steps of the method according to the invention when the computer program is executed in the control unit of the X-ray unit.

The invention also relates to an electronically readable data medium having electronically readable control information stored thereon which comprises at least a computer program according to the invention and is configured in such a manner that it performs the method according to the invention when the data medium is used in a control unit of an X-ray unit.

The X-ray unit according to the invention, the computer program according to the invention and the electronically readable data medium can be further developed with those features which have been explained in relation to the method according to the invention, with the advantages stated there.

Other features which are considered as characteristic for the invention are set forth in the appended claims.

Although the invention is illustrated and described herein as embodied in a method for determining a three-dimensional image data set, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
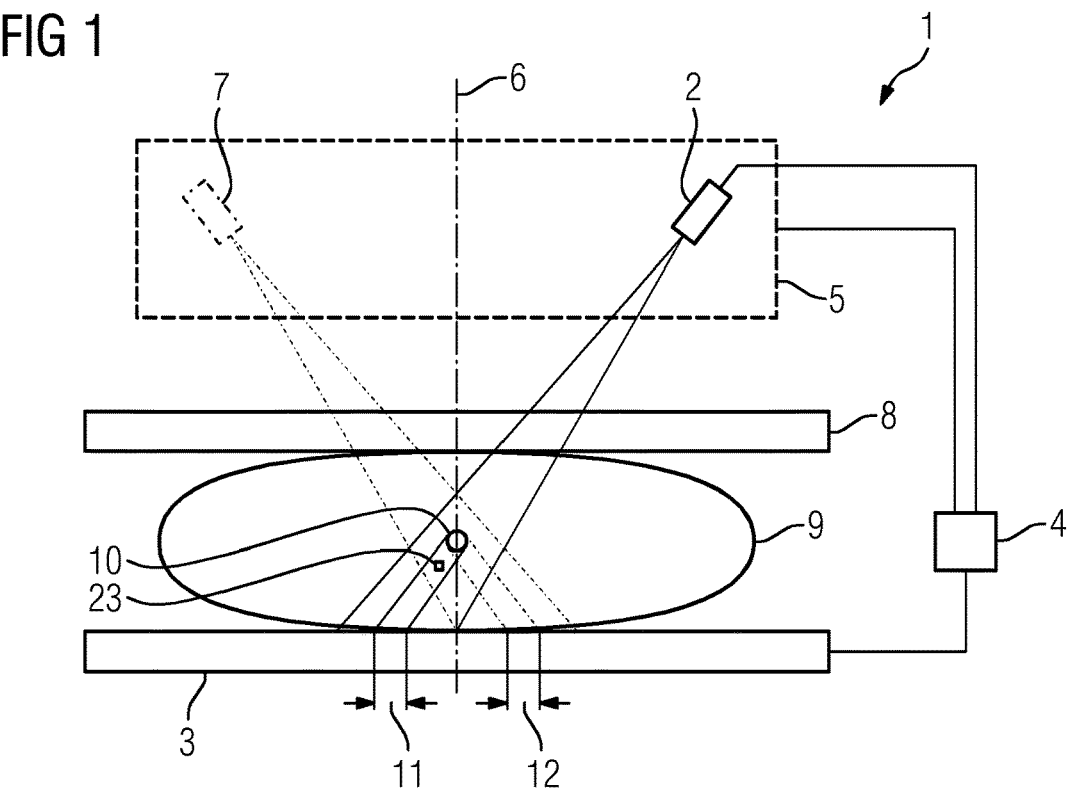
FIG. 1 is a diagrammatic view of an exemplary embodiment of an X-ray unit according to the invention.

Referring now to the figures of the drawing in detail and first, particularly, to FIG. 1 thereof, there is shown an X-ray unit 1 having an imaging facility for capturing projection images of an object under examination 9. The X-ray unit 1 in question is an X-ray unit for performing a 3D mammography, where the object under examination 9 is a breast. The imaging facility comprises an X-ray source 2 and an X-ray detector 3. The X-ray source 2 can be pivoted with respect to a vertical axis 6 by means of a pivoting device 5, illustrated only schematically, driven by a control unit 4 in such a manner that the object under examination 9 can be captured from differing imaging angles. In order to achieve a simple construction of the X-ray unit 1, the detector 3 is fixed. Alternatively it would naturally also be possible to pivot the detector together with the X-ray source 2. In order to reduce a thickness of the tissue to be transirradiated and thereby reduce radiation exposure, a compression plate 8 for compressing the object under examination 9 is furthermore provided.

To demonstrate the change in scanning geometry the X-ray source 2 is additionally illustrated with the associated fan beam in a second exposure position 7.

Figure 3:
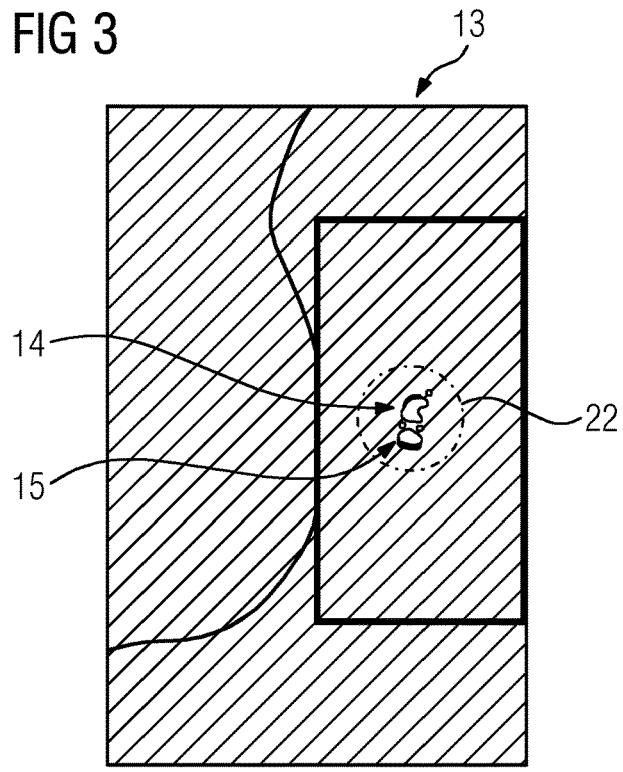
FIG. 3 shows an example of a filtered projection image.

The object under examination 9 can comprise one or more highly absorbent regions 10, for example metal parts or calcifications. During a recording of projection images with differing scanning geometries, the highly absorbent regions 10 are visualized in differing imaging segments 11, 12 of the X-ray detector 3 or of the projection image recorded in each case. Since the X-ray intensity captured changes greatly in the marginal region of said imaging segments 11, 12, marked differences in contrast in the projection images occur in said region. If a three-dimensional image data set is now to be generated from said projection images by means of a filtered backprojection, then the filtering of the projection images, for example with a ramp filter, results in undershoots or oscillations of the intensity in the area surrounding the imaging segment 11, 12. An example of this is illustrated schematically in FIG. 3. A highly absorbent macrocalcification 14 is visualized in the filtered projection image 13. On account of the filtering, undershoots 15 can be recognized in the area surrounding this visualization.

Figure 5:
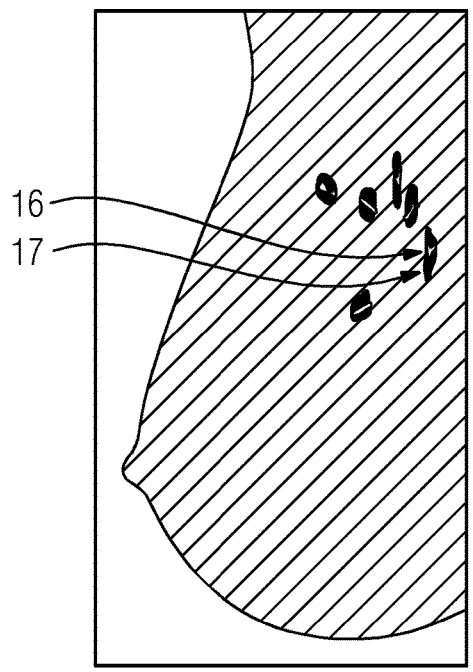
FIGS. 5-10 show slice images of different three-dimensional image data sets, wherein an artifact reduction has in part been performed in accordance with an exemplary embodiment of the method according to the invention.
Figure 7:
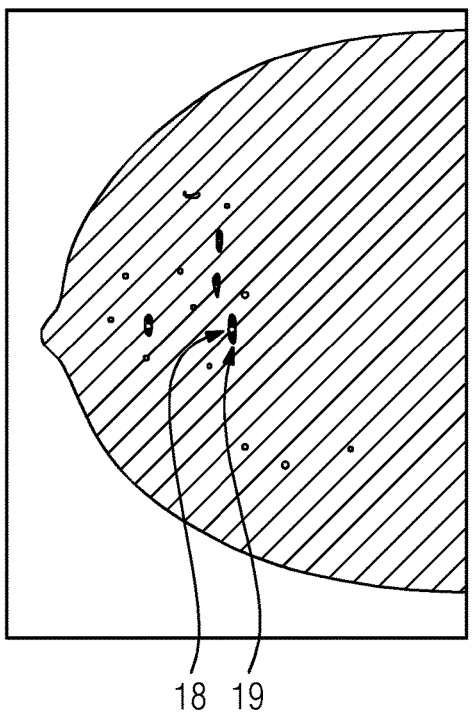

These artifacts in the filtered projection images also result in artifacts in three-dimensional image data reconstructed therefrom. FIGS. 5 and 7 in each case show schematic illustrations of slice images which have been reconstructed from corresponding three-dimensional image data. Metal clips 16 can be seen in FIG. 5. On account of the reconstruction, undershoots 17 arise adjacent to said metal clips which exhibit an absorption behavior strongly differing from the surrounding tissue. As is shown in FIG. 7, a corresponding behavior can also occur for macrocalcifications 18. Undershoots 19 are likewise to be recognized in the area surrounding the macrocalcification 18.

Figure 9:
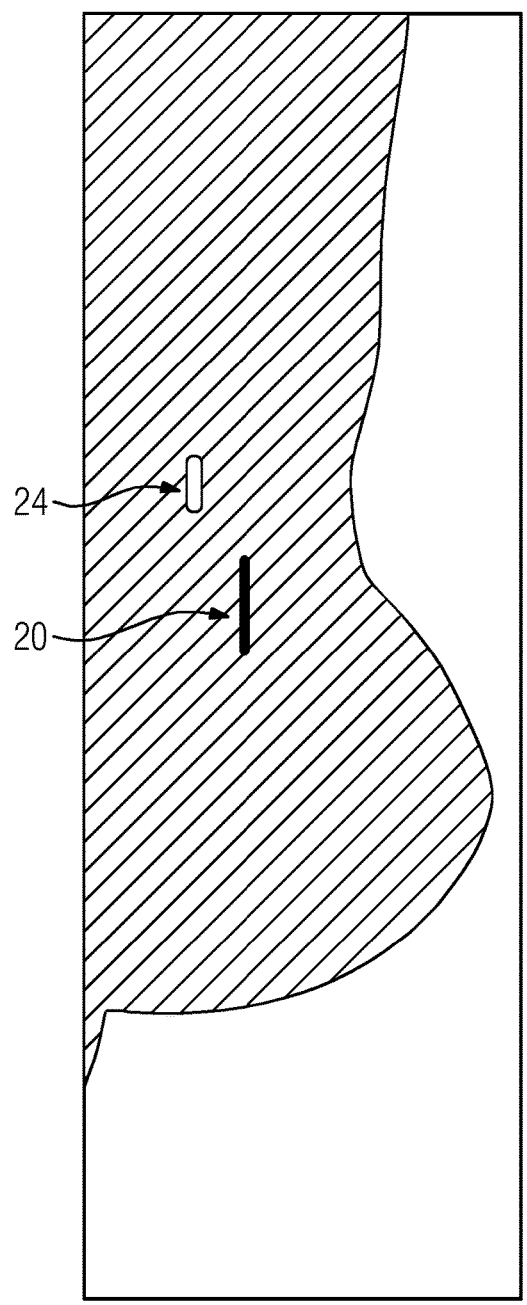

Artifacts resulting from the reconstruction do not occur exclusively in slice images which show the corresponding highly absorbent region 10 but also in adjacent and some even in distant slices. An example of this is illustrated in FIG. 9. FIG. 9 show a schematic illustration of a slice image of a slice which includes no metal parts or macrocalcifications. The filtering of the edges of the imaging segments 11, 12 leads to the formation of stripes 20 in the resulting slice images. In addition, for example in the region 24, light spots occur in the slice images. These occur for voxels for which parts of the projection images indicate the presence of highly absorbent regions which are not actually present. This is the case for example in FIG. 1 for the voxel 23. For the position of the X-ray source 2 shown this lies in the imaging segment 11, but for the exposure position 7 it lies outside the imaging segment 12. A filtered backprojection would thus result in an excessively high apparent absorption for the voxel 23.

Figure 2:
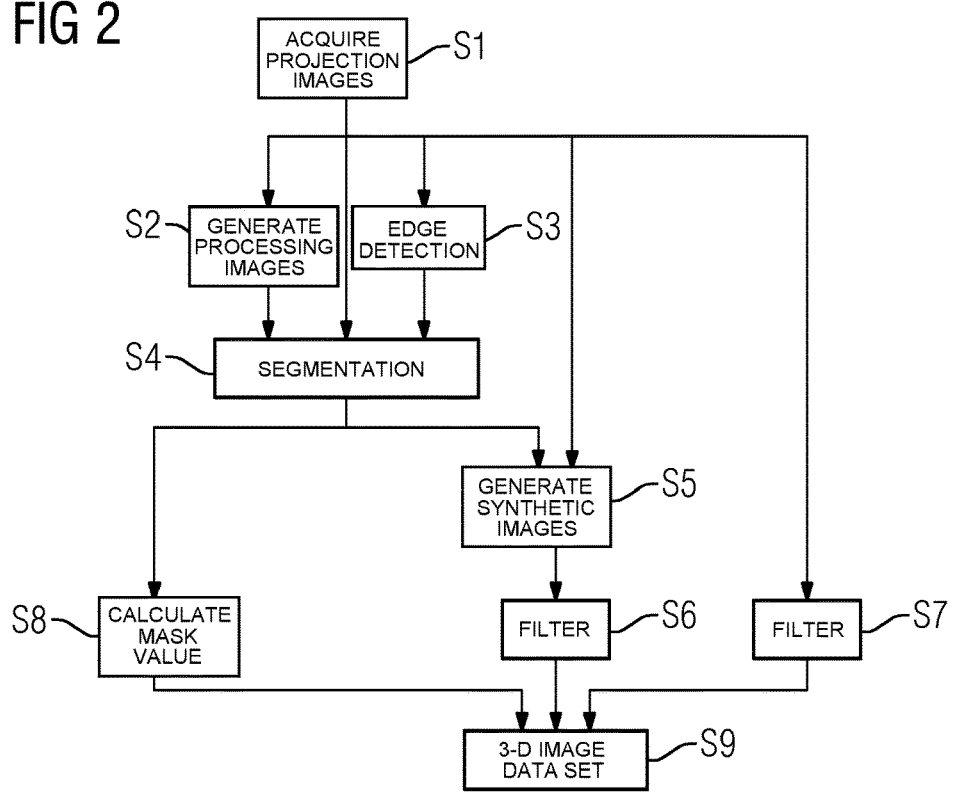
FIG. 2 is a flowchart of an exemplary embodiment of the method according to the invention.

Such artifacts can impede the diagnosis of the recorded images. A control unit 4 which implements a modified method compared with the above for determining a three-dimensional image data set from the projection images is therefore used in the X-ray unit 1. This method will be explained in the following with reference to FIG. 2.

In step S1, as is usual in the prior art, a plurality of projection images of the object under examination 9 are initially recorded from different scanning perspectives. In steps S2 to S5 the imaging segments 11, 12 in said projection images in which a highly absorbent region 10 of the object under examination 9 is visualized are subsequently segmented. For such a segmentation a purely intensity limit value based segmentation is not sufficient as a general rule. Different tissue types exhibit widely differing X-ray absorptions. In addition to the wide variation in intensity due to the relatively small and highly absorbent regions 10 of the object under examination 9 which are to be recognized and segmented, the intensity thus varies over larger areas on account of the differing absorptions in tissue.

In order to nevertheless achieve a robust segmentation, in step S2 a processing image is firstly generated for each of the projection images which corresponds approximately to a background image from which the visualizations of the highly absorbent regions 10 have been removed. This utilizes the fact that the variations in absorption occur at different size scales due to the different tissue types and due to the highly absorbent objects. The visualizations of the highly absorbent regions can therefore be removed from the image data by means of one or more morphological operations. To this end for example an erosion, or a so-called opening operation in which an erosion and a dilation are daisychained, can be applied to the projection images with a suitably chosen structure element. The structure element can be chosen such that on account of its shape and size it is able to remove the visualizations of the highly absorbent regions 10 from the projection images without having too great an influence on larger structures. Morphological operations for image processing are known from the prior art and will therefore not be explained in detail.

A morphological operation is ultimately similar to a convolution of the image with a convolution kernel, for example in the form of a matrix, wherein, instead of a summation using the points adjacent to the point under consideration which are weighted with the matrix entries, in the case of an erosion a minimum and in the case of a dilation a maximum of the weighted adjacent points is chosen. The value of an individual point after the morphological filtering thus depends on its surrounding area, where the size of the structure element defines what proportion of the surrounding area is taken into consideration. In contrast to a filtering for example using a convolution kernel, the value of the point under consideration is however not defined by a weighted sum of the adjacent points but ultimately corresponds to the optionally weighted value of one of said adjacent points, where the selection of this point or value takes place through the morphological operation.

In the exemplary embodiment it should moreover be ensured that a marginal region of the visualization of the highly absorbent region 10 is associated with the imaging segment 11, 12. In order to achieve this, an edge detection in the projection images is performed in step S3 in order to provide an edge image associated with the respective projection image. The segmentation subsequently takes place additionally depending on said edge image. The edge detection can take place for example by means of a Canny algorithm.

In step S4 the projection images are segmented depending both on the processing image provided in step S2 and also on the edge image provided in step S3. Within the scope of the segmentation a mask image in which the pixels belonging to the imaging segment 11, 12 are marked is created for each projection image. In this situation the mask image in question can be a binary image, where for example the value 1 is associated with the pixels belonging to the imaging segment and the value 0 is associated with the other pixels.

For the segmentation, a subtraction image between the projection image and the processing image can firstly be determined in order to subtract from the projection images an image background which describes the variations in intensity due to differing absorptions in tissue. In the resulting image a preliminary segmentation can subsequently take place by means of a limit value comparison, from which a preliminary mask image results. In the preliminary mask image those points can additionally be marked at which an edge has been recognized. It is possible in this situation that a limit value comparison which in particular can relate to limits for gradients or pixel intensities is performed already within the scope of the edge detection or only when the detected edges are transferred, in order to disregard edges which are not to be associated with highly absorbent regions 10, for example skin lines.

With regard to recognized edges which are situated close to a region associated with the imaging segment 11, 12 within the scope of the preliminary segmentation, it can be assumed that said recognized edges constitute the edges of the visualization of the highly absorbent region 10 and should thus be merged with the imaging segment 11, 12. Other edges on the other hand should be discarded. This can be achieved for example by applying a morphological operation, for example a closing operation, with a correspondingly chosen structure element to the preliminary mask image. An initial dilation can connect edges which are situated close to segmented regions thereto. As a result of the following erosion performed within the scope of the closing, edges which have not been connected to another region are removed from the image. Following this operation, there results a final segmentation of the imaging segment 11, 12 and in particular a corresponding mask image.

Optionally those imaging segments which are smaller than a predetermined minimum size, for example a minimum pixel count, can be discarded. This can be expedient because very small highly absorbent regions 10 normally produce no or only negligible artifacts within the scope of the reconstruction of the three-dimensional image data. Discarding these very small segments can thus serve to avoid unnecessary interference with the measurement data.

In step S5, with the aid of the mask image generated in step S4 an associated synthetic image is generated for each of the projection images. The image data of the synthetic image outside the imaging segment corresponds to the image data of the associated projection image. Within the imaging segment the image data is set to predetermined values which are predetermined such that an interpolation between a plurality of pixels adjacent to the imaging segment is firstly performed in order to adapt the intensity in the modified imaging segment to the surroundings. Subsequently a noise signal is added to these preliminary values in order to adjust the noise in the modified imaging segment to the surroundings.

Figure 4:
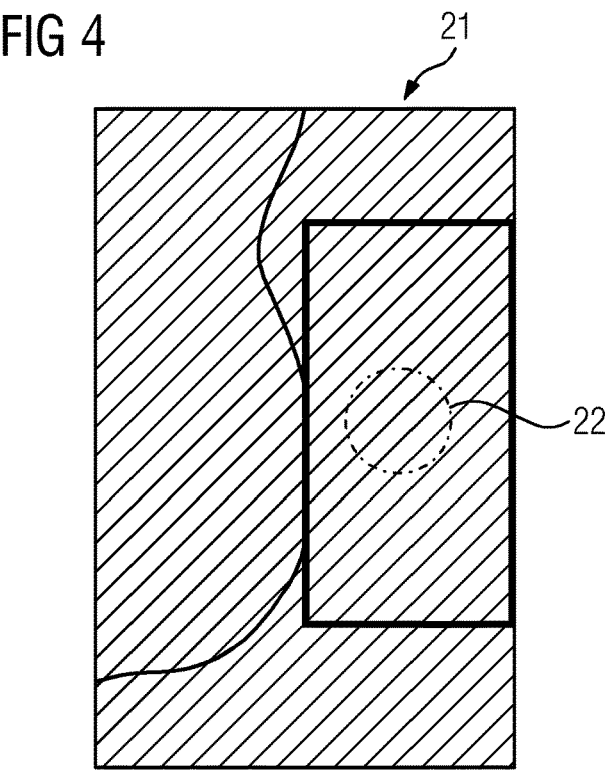
FIG. 4 shows an example of a filtered synthetic image.

The projection images and the synthetic images are filtered separately from one another in steps S6 and S7. The filtering therefore takes place, as is usual in the case of filtered backprojections, for example with a ramp filter. An example of a filtered projection image 13 is shown schematically in FIG. 3. FIG. 4 schematically shows the associated filtered synthetic image 21. The region 22 in which the visualizations of the macrocalcification 14 and the undershoots 15 resulting from the filtering are situated in the filtered projection image 13 is essentially smooth in the filtered synthetic image because the visualization of the macrocalcification 14 has been removed as a result of the segmentation of the imaging segment 11, 12 and the subsequent population of the imaging segment 11, 12 with predetermined values and thus the undershoots originating from the filtering of said visualization also do not occur.

In step S8 the mask images are backprojected in order to calculate a mask value for each voxel of a three-dimensional image data set to be calculated. If as explained above the mask image is set to one for pixels in the imaging segment 11, 12 and for other pixels to zero and if the backprojection took place in such a manner that each voxel depends in each case on only one pixel of a respective projection image, then said backprojection equates to counting in how many of the projection images the respective relevant pixel is located in a respective imaging segment. In the case of an ideal imaging a voxel which is actually located in a highly absorbent region 10 of the object under examination 9 would have to be located in a respective imaging segment 11, 12 in all the projection images. On account of noise and imaging errors it is however also possible that the relevant point in individual projection images is not located in an imaging segment 11, 12. As explained in the following, this will be taken into consideration with regard to the reconstruction.

The three-dimensional image data set is determined in step S9, wherein the image data of the respective voxel is determined by backprojection of the relevant pixels of the filtered projection images when the selection condition dependent on the mask value of said voxel is satisfied, and by backprojection of the relevant pixels of the filtered synthetic images when the selection condition is not satisfied. The selection condition compares the mask value with a limit value which for example can be chosen such that the selection condition is satisfied when the relevant pixel of the respective projection image is situated in an imaging segment 11, 12 for 80% of the projection images. In this case it can be assumed that the corresponding voxel actually maps a highly absorbent region 10, which is why the original projection images which also actually map this highly absorbent region 10 are used for the reconstruction of this voxel. If the selection condition is not satisfied, then it is assumed that the corresponding voxel does not map a highly absorbent region 10. The synthetic images can therefore be used for the reconstruction of said voxel. These likewise depict all the other regions of the object under examination but exhibit fewer artifacts, whereby an improved image quality can be achieved overall.

The use of the selection condition can moreover prevent artifacts occurring for voxels which are situated only in one or a few projection images in the imaging segment. For example, it can be seen from FIG. 1 for the voxel 23 that it is not situated in a highly absorbent region. Since synthetic images are used for the reconstruction in this case, an influence of highly absorbent regions and thus an imaging error are suppressed.

Figure 6:
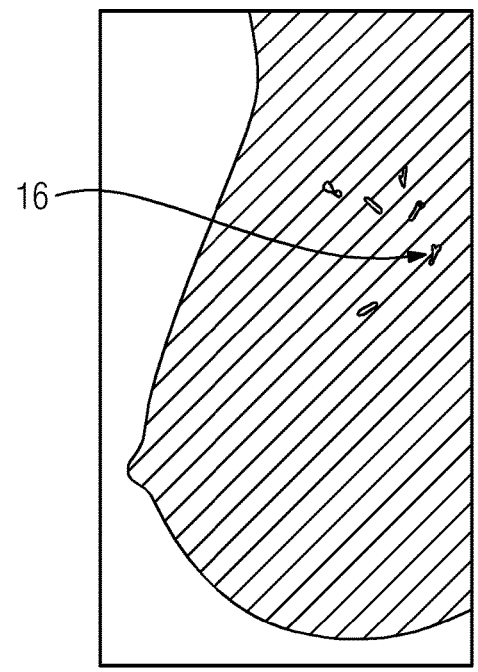
Figure 8:
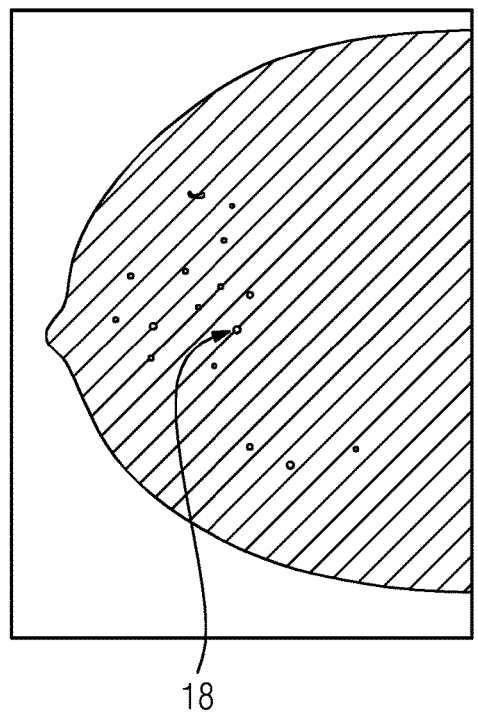
Figure 10:
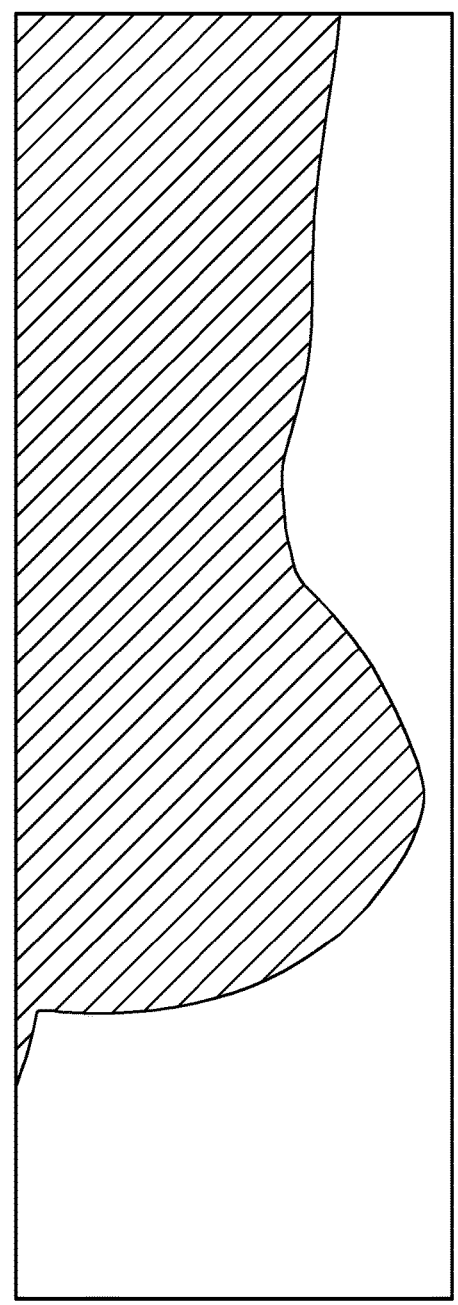

Examples of the improvements achieved are shown schematically in FIGS. 6, 8 and 10, wherein the slice image shown in FIG. 6 corresponds to the comparison slice image in FIG. 5 reconstructed by means of a conventional filtered backprojection, the slice image shown in FIG. 8 corresponds to the comparison slice image in FIG. 7 reconstructed by means of a conventional filtered backprojection and the slice image shown in FIG. 10 corresponds to the comparison slice image in FIG. 9 reconstructed by means of a conventional filtered backprojection. The same projection images have been used in each case for the reconstruction. As can be seen by a comparison of FIGS. 5 and 6 or 7 and 8, the undershoots 17, 19 shown in FIGS. 5 and 7 are not present in FIGS. 6 and 8, whereby the image quality is increased overall. The stripes 20 and light regions 24 which can be seen in FIG. 9 are also not present in FIG. 10. The described procedure thus results in a considerable improvement in the image quality of the resulting slice images.

The described method can also exist in the form of a computer program which implements the method on the control unit 4 of a magnetic resonance device shown in FIG. 1 when it is executed on said control unit 4. An electronically readable data medium, or computer-readable medium with electronically readable control information stored thereon can also be present, which control information comprises at least the described computer program and is configured such that it performs the described method when the data medium is used in the control unit 4 of the magnetic resonance device 1.

Although the invention has been illustrated and described in detail by means of the preferred exemplary embodiment, the invention is not restricted by the disclosed examples and other variations can be derived therefrom by the person skilled in the art without departing from the scope of protection of the invention.

The following is a summary list of reference numerals and the corresponding structure used in the above description of the invention:

1 X-ray unit
2 X-ray source
3 X-ray detector
4 Control unit
5 Pivoting device
6 Vertical axis
7 Exposure position
8 Compression plate
9 Object under examination
10 Region
11 Imaging segment
12 Imaging segment
13 Projection image
14 Macrocalcification
15 Undershoot
16 Metal clip
17 Undershoot
18 Macrocalcification
19 Undershoot
20 Stripes
21 Synthetic image
22 Region
23 Voxel
24 Region
S1 to S9 Method Steps

The invention claimed is:

1. A method for determining a three-dimensional image data set from a plurality of two-dimensional projection images of an object under examination, the method comprising the following steps:
 applying at least one morphological operation to each projection image in order to provide a processing image respectively associated with each projection image;
 segmenting at least one respective imaging segment, in which a highly absorbent region of the object under examination is mapped in a respective projection image, depending on the processing image associated with the projection image, and creating a mask image associated with the respective projection image, in which pixels belonging to the imaging segment are marked;
 generating an associated synthetic image for each projection image, the image data of which outside the imaging segment corresponds to the image data of the associated projection image and the image data of which within the imaging segment is set to predetermined values;
 separately filtering the projection images and the synthetic images;
 determining the three-dimensional image data set by backprojecting the mask images in order to determine a mask value for each voxel of the image data set, wherein the image data of the respective voxel are determined by a backprojection of the relevant pixels of the filtered projection images when a selection condition dependent on the mask value of the voxel is satisfied, and by a backprojection of the relevant pixels of the filtered synthetic images when the selection condition is not satisfied.

2. The method according to claim 1, wherein the selection condition is satisfied when for at least a predetermined number of projection images the pixels of the respective projection image which are relevant to the calculation of the image data of the voxel are situated within the respective imaging segment, the predetermined number being less than a total number of projection images.

3. The method according to claim 1, which comprises predetermining the values to which the image data of the synthetic image are set within the imaging segment by superimposing a noise signal on predetermined initial values for individual pixels in the imaging segment.

4. The method according to claim 1, which comprises predetermining the values to which the image data of the synthetic image are set within the imaging segment or the initial values depending on image data of at least one pixel, adjacent the imaging segment, of the associated projection image.

5. The method according to claim 1, which comprises performing an edge detection in the projection images in order to provide an edge image associated with the respective projection image, and wherein the step of segmenting the imaging segment takes place depending on the edge image associated with the respective projection image.

6. The method according to claim 1, wherein the step of segmenting the imaging segments comprises exclusively segmenting imaging segments that have a predetermined minimum size.

7. The method according to claim 1, which comprises acquiring the projection images within a tomosynthesis process.

8. The method according to claim 7, which comprises acquiring the projection images within the scope of a 3D mammography process.

9. The method according to claim 1, which comprises recording the projection images at various imaging angles with respect to the object under examination and thereby sweeping an imaging angle range of less than 90°.

10. The method according to claim 9, which comprises sweeping an imaging angle range of less than 60° in recording the projection images at the various imaging angles.

11. The method according to claim 1, which comprises producing a two-dimensional image display depending on the three-dimensional image data set and graphically highlighting a highly absorbent region in the two-dimensional image display.

12. An X-ray unit, comprising:
 an imaging facility for acquiring projection images of an object under examination from a plurality of imaging angles; and
 a control unit connected to said imaging facility and configured to carry out the method according to claim 1.

13. A non-transitory computer readable medium comprising a computer program to be loaded directly into a memory of a control unit of an X-ray unit, having program resources configured to perform the steps of the method according to claim 1 when the computer program is executed in the control unit of the X-ray unit.

14. An non-transitory electronically readable data medium having electronically readable control information stored thereon, the control information including a computer program to be loaded directly into a memory of a control unit of an X-ray unit, the computer program including program code configured to cause the control unit and the X-ray unit to perform the method according to claim 1 when data medium is used in the control unit of the X-ray unit.

\* \* \* \* \*